US009706963B2

(12) United States Patent
Gupta et al.

(10) Patent No.: US 9,706,963 B2
(45) Date of Patent: Jul. 18, 2017

(54) HETEROGENEOUS MULTI-CORE PROCESSING SYSTEMS AND DATA ROUTING METHODS FOR HIGH-THROUGHPUT MODEL PREDICTIVE MEDICAL SYSTEMS

(71) Applicants: Sandeep Gupta, Phoenix, AZ (US); Ayan Banerjee, Tempe, AZ (US)

(72) Inventors: Sandeep Gupta, Phoenix, AZ (US); Ayan Banerjee, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 282 days.

(21) Appl. No.: 14/573,802

(22) Filed: Dec. 17, 2014

(65) Prior Publication Data
US 2015/0164432 A1    Jun. 18, 2015

Related U.S. Application Data

(60) Provisional application No. 61/917,191, filed on Dec. 17, 2013.

(51) Int. Cl.
| | |
|---|---|
| G01N 33/48 | (2006.01) |
| G01N 33/50 | (2006.01) |
| A61B 5/00 | (2006.01) |
| A61B 5/145 | (2006.01) |
| G06F 19/28 | (2011.01) |
| A61M 5/172 | (2006.01) |
| A61M 5/142 | (2006.01) |

(52) U.S. Cl.
CPC .......... *A61B 5/7275* (2013.01); *A61B 5/0024* (2013.01); *A61B 5/14546* (2013.01); *G06F 19/28* (2013.01); *A61M 5/1723* (2013.01); *A61M 2005/14208* (2013.01); *A61M 2230/04* (2013.01); *A61M 2230/201* (2013.01); *A61M 2230/205* (2013.01); *A61M 2230/30* (2013.01)

(58) Field of Classification Search
None
See application file for complete search history.

(56) References Cited

U.S. PATENT DOCUMENTS

| | | | | |
|---|---|---|---|---|
| 2007/0178160 | A1* | 8/2007 | Burnett | A61B 5/14539 424/484 |
| 2009/0202240 | A1* | 8/2009 | Carroll | H04J 14/0227 398/45 |

OTHER PUBLICATIONS

"Intel website for MIC" http://www.intel.com/content/www/us/en/processors/xeon/xeon-phi-detail.html. Oct. 2013.*

D.R. Wada et al., "The Hybrid Model: A New Pharmacokinetic Model for Computer-Controlled Infusion Pumps", IEEE Transactions on Biomedical Engineering, vol. 41, No. 2, pp. 134-142, 1994.
R. Hovorka et al., "Overnight Closed-Loop Insulin Delivery in Young People With Type 1 Diabetes: A Free-Living, Randomized Clinical Trial", Diabetes Care vol. 37, pp. 1204-1211, 2014.
S.L. Shafer et al., "Algorithms to rapidly achieve and maintain stable drug concentrations at the site of drug effect with a computer-controlled infusion pump," Journal of Pharmacokinetics and Pharmacodynamics, vol. 20, pp. 147-169, 1992. * Please obtain copy—http://link.springer.com/article/10.1007%2FBF01070999 *.
J. Zhang et al., "cuBLASTP: Fine-Grained Parallelization of Protein Sequence Search on a GPU", in IEEE International Parallel and Distributed Processing Symposium, Phoenix, Arizona, May 2014.
D.R. Horn et al.,"Interactive k-d tree gpu raytracing," in Proceedings of the 2007 Symposium on Interactive 3D Graphics and Games, ser. I3D '07. pp. 167-174, 2007.
Y. Guo et al., "How well do graph-processing platforms perform? An empirical performance evaluation and analysis," in IEEE International Parallel and Distributed Processing Symposium, Phoenix, Arizona, USA, May 2014.
F. Checconi et al., "Traversing trillions of edges in real-time: Graph exploration on large-scale parallel machines," in IEEE International Parallel and Distributed Processing Symposium, Phoenix, Arizona, USA, May 2014.
M. Deveci et al., "Exploiting geometric partitioning in task mapping for parallel computers," in IEEE International Parallel and Distributed Processing Symposium, Phoenix, Arizona, USA, May 2014.
R.S. Brock et al., "Evaluation of a parallel fdtd code and application to modeling of light scattering by deformed red blood cells," Opt. Express, vol. 13, No. 14, pp. 5279-5292, 2005.
J. Pereda, et al., "Fdtd analysis of magnetized ferrites: application to the calculation of dispersion characteristics of ferrite-loaded waveguides," Microwave Theory and Techniques, IEEE Transactions on, vol. 43, No. 2, pp. 350-357, 1995.

(Continued)

*Primary Examiner* — Russell S Negin
(74) *Attorney, Agent, or Firm* — Michael Best & Friedrich LLP

(57) ABSTRACT

A heterogeneous multiple core control system for predictive medical monitoring is provided. The system includes a first processor platform that is optimized for serialized computation and a second processor platform that is optimized for parallelized computation. A memory stores instructions that are executed by either the first processor platform or the second processor platform to provide the functionality of the system. By executing the instructions, the system determines whether a condition of a first patient is to be monitored using a primarily parallelized model or a primarily serialized model. The predicted condition is calculated using the primarily parallelized model by executing the primarily parallelized model on the second processor platform. The predicted condition is calculated using the primarily serialized model by executing the primarily serialized model on the first processor platform.

20 Claims, 16 Drawing Sheets

(56) References Cited

OTHER PUBLICATIONS

L.-K. Wu et al., "Fdtd analysis of the radiometric temperature measurement of a bilayered biological tissue using a body-contacting waveguide probe," Microwave Theory and Techniques, IEEE Transactions on, vol. 43, No. 7, pp. 1576-1583, 1995.

T.L. Jackson et al., "A mathematical model to study the effects of drug resistance and vasculature on the response of solid tumors to chemotherapy," Mathematical Biosciences, vol. 164, No. 1, pp. 17-38, 2000.

S.-H. Sun et al., "A new subgridding scheme for two-dimensional fdtd and fdtd (2,4) methods," IEEE Transactions on Mag-netics,, vol. 40, No. 2, pp. 1041-1044, 2004.

M. Pore et al., "Performance trends of multicore system for throughput computing in medical application", IEEE Conference on High Performance Computing—2nd Workshop on Performance Engineering and Applications (WPEA), 2013.

M. Pore et al., "Heterogeneous many cores for medical control: Performance, Scalability, and Accuracy", IEEE Conference on High Performance Computing, Goa, India, Dec. 2014.

M. Pore et al., "Performance evaluation of multi core systems for high throughput medical applications involving model predictive control", IEEE Conference on High Performance Computing, Goa, India, Dec. 2014.

K. Lesh et al., "Medical Device Interoperability—Assessing the Environment", In HCMDSS-MDPnP. Joint Workshop on, pp. 3-12, 2007.

H. Scherl et al., "Fast gpu-based ct reconstruction using the common unified device architecture (CUDA)", In Nuclear Science Symposium Conference Record, 2007. NSS '07. IEEE, vol. 6, pp. 4464-4466, 2007.

J. Thiyangalingam et al., "On the usage of gpus for efficient motion estimation in medical image sequences. Journal of Biomedical Imaging," 2011:1:1-1:15, 2011.

Y.-H. Chen et al., "Sub-microwatt Correlation Integral Processor for Implantable Closed-loop Epileptic Neuromodulator", Proceedings of 2010 IEEE International Symposium on Circuits and Systems (ISCAS), pp. 2083-2086, 2010.

T.-J. Chen et al., "The Implementation of a Low-Power Biomedical Signal Processor for Real-Time Epileptic Seizure Detection on Absence Animal Models", IEEE Journal on Emerging and Selected Topics in Circuits and Systems, vol. 1, No. 4, pp. 613-621, 2011.

C.-Y. Chiang et al., "Seizure Prediction Based on Classification of EEG Synchronization Patterns with On-line Retraining and Post-Processing Scheme", in Proceedings of IEEE Conference of Engineering in Medicine and Biology Society (EMBC 2011), Boston, USA, 2011.

\* cited by examiner

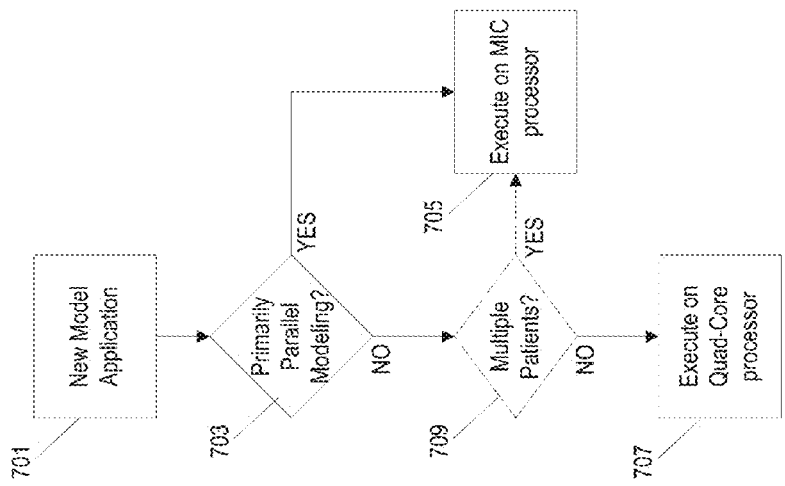
FIG. 7
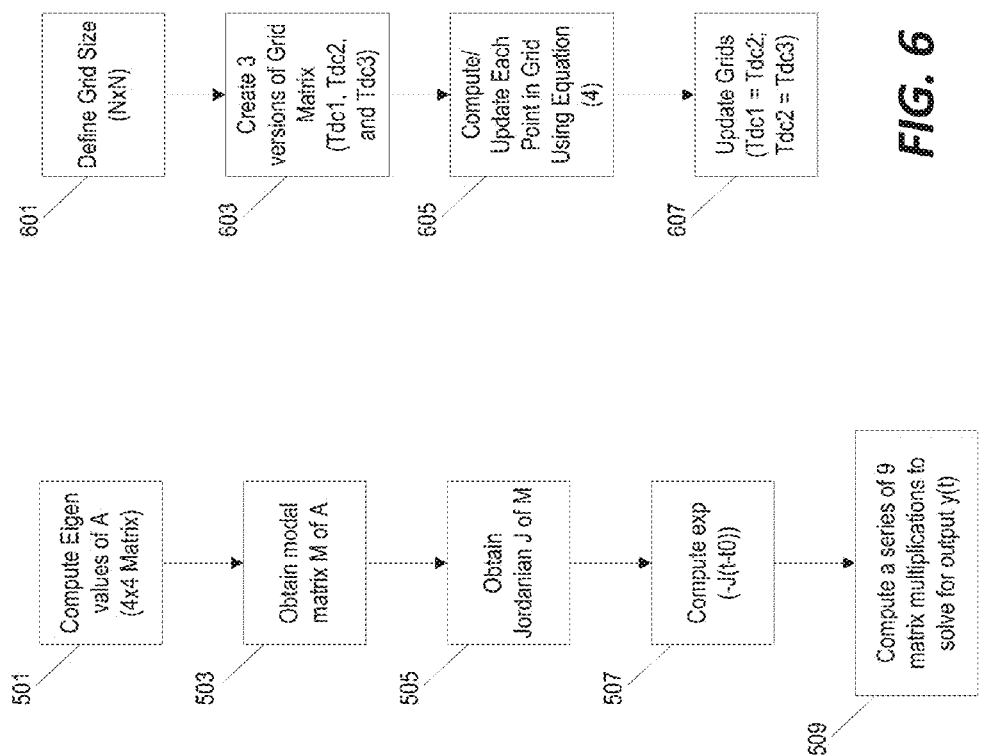
FIG. 6
FIG. 5

| Number of patients | Execution Time (GPU) | Execution time (MIC) | Execution time i7 |
|---|---|---|---|
| 1 | 213 | 84.85 | 5.58 |
| 2 | 992 | 89.02 | 6.26 |
| 4 | 2081 | 94.92 | 7.48 |
| 8 | 2584 | 118.36 | 13.11 |
| 16 | 3552 | 240.73 | 24.78 |
| 32 | | 2066.99 | 53.86 |
| 64 | | | 336.81 |

| Gridsize 64 × 64 | | | | | |
|---|---|---|---|---|---|
| #patients | i7 (s) | MIC (s) | GPU | | |
| | | | w/ communication (s) | computation only w/ neighbor (s) | computation only w/o neighbor (s) |
| 1 | 0.440 | 0.024 | 26 | 1 | 1 |
| 2 | 0.434 | 0.010 | 61 | 1 | 1 |
| 4 | 0.414 | 0.016 | 82 | 4 | 2 |
| 8 | 0.413 | 0.052 | 166 | 6 | 4 |
| 16 | 0.417 | 0.109 | 327 | 12 | 9 |
| 32 | 0.603 | 0.232 | 661 | 25 | 17 |
| 64 | 1.303 | 0.576 | 1363 | 60 | 47 |

FIG. 9

| Gridsize 256 × 256 | | | | | |
|---|---|---|---|---|---|
| #patients | i7 (s) | MIC (s) | GPU | | |
| | | | with communication (s) | computation only w/ neighbor (s) | computation only w/o neighbor (s) |
| 1 | 9 | 0.0231 | 83 | 3 | 1 |
| 2 | 10 | 0.0145 | 94 | 6 | 2 |
| 4 | 10 | 0.0161 | 293 | 12 | 5 |
| 8 | 11 | 0.0448 | 541 | 24 | 9 |
| 16 | 13 | 0.0999 | 993 | 47 | 19 |
| 32 | 15 | 0.2797 | 1953 | 95 | 36 |
| 64 | 32 | 1.1762 | 3823 | 190 | 73 |
| 128 | | 4.9340 | | | |

FIG. 10

FIG. 12 sample: Number of patients =16

| function | FLOPs | | Energy(KILOJoule) | | | Performance (MFLOPS/KJ) | |
|---|---|---|---|---|---|---|---|
| | | i7 | MIC | i7 | GPU | MIC | GPU |
| eigen | 36 | 0.342 | 3.50 | 125.0 | 66.35 | 10.29 | 0.2864 |
| mmul | 286.7 | 1.080 | 14.11 | 503.7 | 265.4 | 20.32 | 0.5692 |
| datatransfer | | 1.145 | 130.71 | 1534.0 | | | |

FIG. 13 sample: Gridsize 256 × 256

| #patients | TFLOPs | | Energy(kJ) | | | Performance (TFLOPS/kJ) | |
|---|---|---|---|---|---|---|---|
| | | i7 | MIC | i7 | GPU | MIC | GPU |
| 1 | 0.713 | 1.756 | 0.0023 | 5.751 | 0.4061 | 307.50 | 0.1240 |
| 2 | 1.426 | 3.039 | 0.0023 | 8.071 | 0.3918 | 615.70 | 0.1767 |
| 4 | 2.852 | 4.693 | 0.0028 | 17.12 | 0.6078 | 1008.10 | 0.1666 |
| 8 | 5.704 | 6.841 | 0.0058 | 33.27 | 0.8338 | 986.20 | 0.1715 |
| 16 | 11.41 | 10.32 | 0.0113 | 64.18 | 1.105 | 1008.00 | 0.1777 |
| 32 | 22.82 | 22.33 | 0.0310 | 128.4 | 1.022 | 735.20 | 0.1777 |
| 64 | 45.63 | 44.78 | 0.0999 | 259.2 | 1.019 | 456.60 | 0.1760 |
| 128 | 91.27 | | 0.3821 | | | 238.90 | |

HETEROGENEOUS MULTI-CORE PROCESSING SYSTEMS AND DATA ROUTING METHODS FOR HIGH-THROUGHPUT MODEL PREDICTIVE MEDICAL SYSTEMS

CROSS-REFERENCE TO RELATED APPLICATIONS

This application claims priority to U.S. Provisional Application No. 61/917,191, filed Dec. 17, 2013, and titled "HIGH THROUGHPUT MODEL PREDICTIVE CONTROLLER," the entirety of which is incorporated herein by reference.

STATEMENT REGARDING FEDERALLY SPONSORED RESEARCH OR DEVELOPMENT

This invention was made with government support under grant No. 0834797 awarded by the National Science Foundation. The government has certain rights in the invention.

BACKGROUND

The present invention relates to medical control systems that process feedback from physiological monitors and provide real-time inputs to actuators that control a physiological state of a patient (e.g., medication infusion pumps).

SUMMARY

Multicore parallel processing computing systems can provide increased throughput for certain medical operations such as, for example, medical treatment planning applications. Medical applications such as radiotherapy, MRI, and CT scan may utilize fast graphics processing units (GPUs) for high performance processing of sophisticated high resolution images or solving complex higher order differential equations for diagnosis and treatment of physiological disorders.

Multicore parallel processing may also provide benefits for real-time medical control systems (RTMCSes) that perform high throughput computations to process feedback from physiological monitors and to provide real time inputs to actuators for high precision control of a physiological state of a patient. For example, in high intensity focused ultrasound (HIFU), the MRI image of the tissue is processed and the temperature rise of the tissue is provided as real time feedback to the controller that controls the intensity of the ultrasound. The throughput requirement further increases when the RTMCS supports multiple patients—either by design or in the event of a disaster scenario.

In a remote controlled infusion pumps, the drug diffusion dynamics are monitored and the rate of drug infusion is controlled based on a feedback mechanism. In some such systems, the drug diffusion dynamics are simulated for 1 hour into the future to provide model-estimated blood glucose concentration as feedback for determining optimal insulin infusion in the present. Such modeling requires sophisticated processing to be performed within seconds in order to determine future actions. However, as discussed in further detail below, the modeling techniques lack inherent parallelism that would naturally lend itself to implementation on a high-throughput parallel processing platform.

Various embodiments of the invention described herein provide a multicore parallel processing computing system for model-predictive medical applications that includes cores with different computation capabilities and energy consumption within the same system. The computing system routes model-predictive operations to a specific processing core platform based on conditions such as modeling technique and current system load.

In one embodiment, the invention provides a heterogeneous multiple core control system for predictive medical monitoring. The system includes a first processor platform that is optimized for serialized computation and a second processor platform that is optimized for parallelized computation. A memory stores instructions that are executed by either the first processor platform or the second processor platform to provide the functionality of the system. By executing the instructions, the system determines whether a condition of a first patient is to be monitored using a primarily parallelized model or a primarily serialized model. The predicted condition is calculated using the primarily parallelized model by executing the primarily parallelized model on the second processor platform. The predicted condition is calculated using the primarily serialized model by executing the primarily serialized model on the first processor platform.

In some embodiments, the system balances the workload between the first processor platform and the second processor platform such that the predicted condition is calculated using the primarily serialized model by executing the primarily serialized model on the second (i.e., primarily parallelized) processor platform when doing so would result in lower average execution times. In some embodiments, the system is configured to route execution of the primarily serialized model to the second processor platform when a total number of patients being monitored using the primarily serialized model exceeds a threshold.

Other aspects of the invention will become apparent by consideration of the detailed description and accompanying drawings.

BRIEF DESCRIPTION OF THE DRAWINGS

FIG. 5 is a flowchart of a method for predicting drug diffusion dynamics on the system of FIG. 1 using a primarily serialized, but computationally less-complex, modeling algorithm.

FIG. 6 is a flowchart of a method for predicting drug diffusion dynamics on the system of FIG. 1 using a more parallelized, but computationally more complex, modeling algorithm.

FIG. 7 is a flowchart of a method for assigning model-predictive operations to either the processing component of FIG. 4B or the processing component of FIG. 4D based on the modeling algorithm to be utilized and current system load.

FIG. 9 is a table of measured execution times for the predictive algorithm of FIG. 6 using a grid-size of 64×64 by various processing platforms for various numbers of patients.

FIG. 10 is a table of measured execution times for the predictive algorithm of FIG. 6 using a grid-size of 256×256 by various processing platforms for various numbers of patients.

FIG. 12 is a table of energy and performance metrics for various processing platforms each monitoring multiple patients and executing the predictive algorithm of FIG. 5.

FIG. 13 is a table of energy and performance metrics for various processing platforms each executing the predictive algorithm of FIG. 6 for varying numbers of patients.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
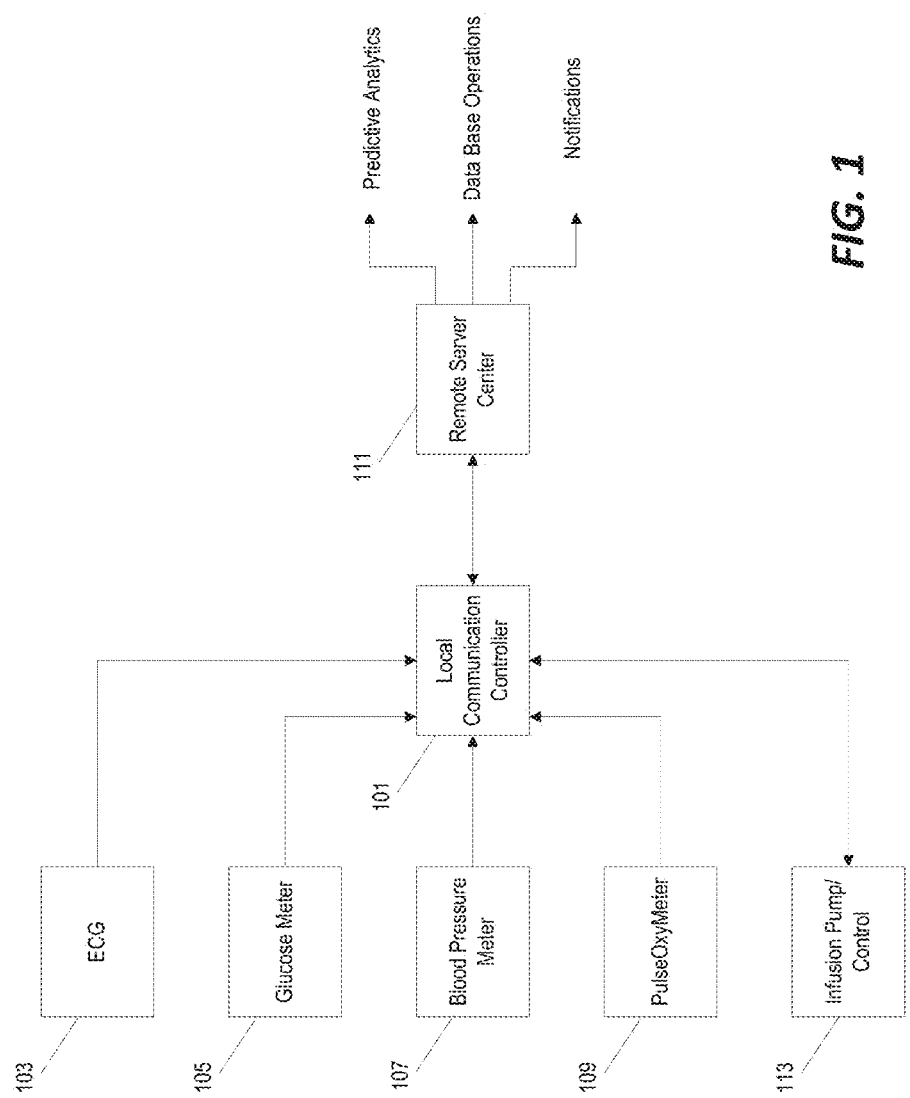
FIG. 1 is a block diagram of a patient monitoring and feedback control system.

FIG. 1 illustrates one example of a patient monitoring system. A local communication controller 101 is coupled to various patient monitoring systems such as, for example, an ECG system 103, a glucose meter 105, a blood pressure meter 107, and a pulse oxymeter 109. The local controller 101 is also coupled to one or more actuator system such as, for example, an infusion pump controller 113. The local controller 101 receives signals from each of the local monitoring systems and transmits various data to a remote server center 111. The remote server center 111 processes the data and provides predictive analytics, data base operations, and various notifications. In some constructions, the remote server center 111 also determines updated actuator settings that are transmitted through to the local communication controller 101 and used, for example, to control the operation of the infusion pump 113.

In some constructions, a single remote processing server 111 can be used to process data and provide control outputs for numerous patients at the same time. In still other constructions, the multiple remote processing servers 111 can be used each monitoring a defined number of patients. When emergency conditions exist (such as, for example, power failures), patients that would be monitored by a failing remote server can be routed to a remote processing server 111 that is still operational.

In hospitals, patients are continuously monitored for vital signs or physiological parameters such as heart rate and body temperature using various sensor (such as illustrated in FIG. 1). For critical patients, data collected is used by control algorithms to finely monitor certain physiological parameters such that they do not exceed a predefined threshold value. If the signal is estimated to exceed the threshold, an alarm may be generated or the drug infusion rate of the infusion pump may be adjusted. In order to more accurately predict the result of adjustments to the actuator settings, some systems will implement a feedback-based model predictive control (MPC) algorithm.

Figure 2:
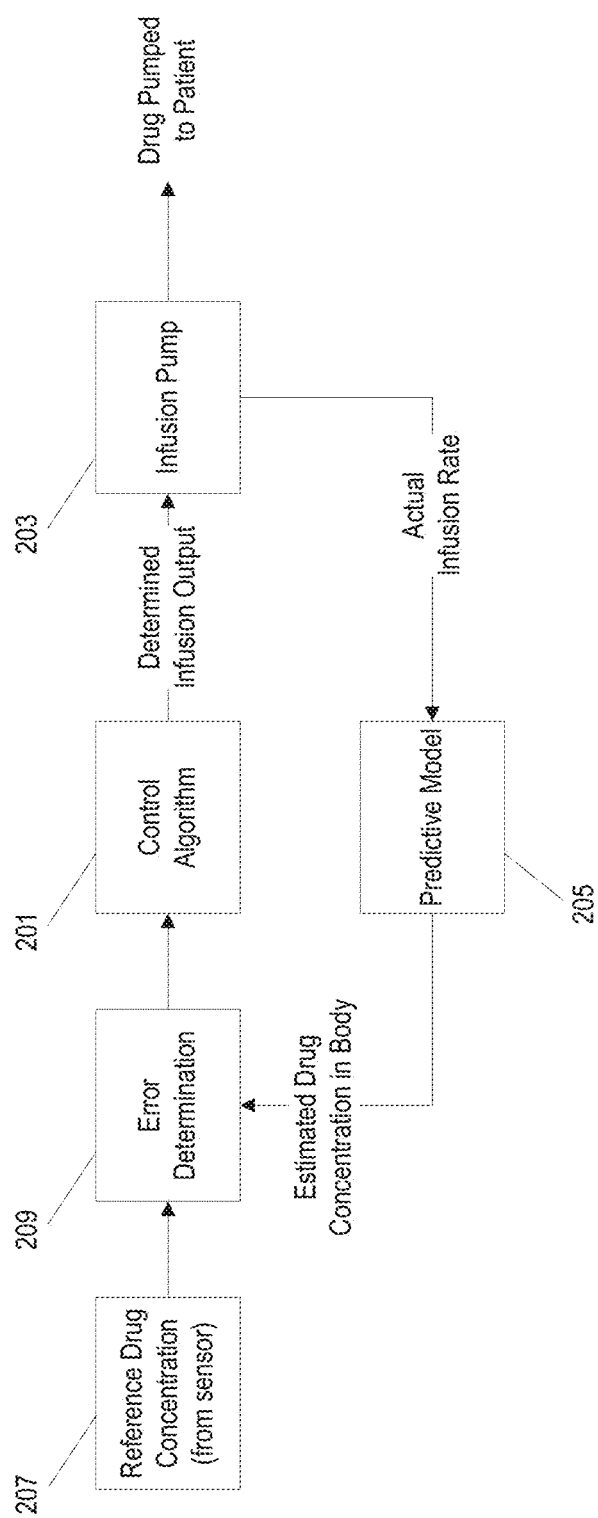
FIG. 2 is a flowchart of a feedback control mechanism implemented by the system of FIG. 1.

FIG. 2 illustrates an example of a feedback mechanism implemented by the remote processing server 111 for regulating and updating an actuator setting for the infusion pump 113. A control algorithm is used to determine a infusion pump actuator setting (step 201) and the system provides the actuator setting to the infusion pump (step 203), which pumps a drug to a patient. A predictive model (step 205) is used to simulate the infused drug in feedback in order to estimate drug levels in the body. This estimated drug concentration is then compared to a reference drug level (step 207) and the control error (step 209) is used by the control algorithm (step 201) to adjust the infusion rate.

Model predictive control systems—such as those illustrated in FIGS. 1 and 2—may provide various models of different complexity that predict an output with different accuracy. More complex models require more computational resources. However, these applications are time critical because every few seconds the infusion rate is adjusted based on the feedback of predictive model. Some MPC-based medical applications may use a simple Kalman filter type linear predictor model. However, such predictions are not accurate and inaccurate estimation of models may cause overshoots and undershoots in the control operation which can be severely harmful for the patient. For example, frequent hypoglycemia caused by an "undershoot" in glucose concentration may lead to blindness.

Figure 3A:
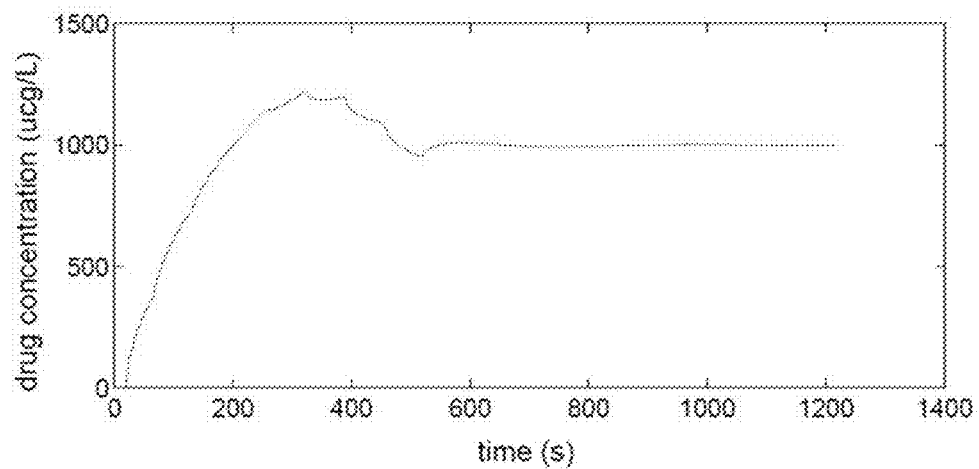
FIG. 3A is a graph of drug concentration in human blood over time as controlled by a pharmacokinetic model-based control algorithm implemented by the system of FIG. 1.
Figure 3B:
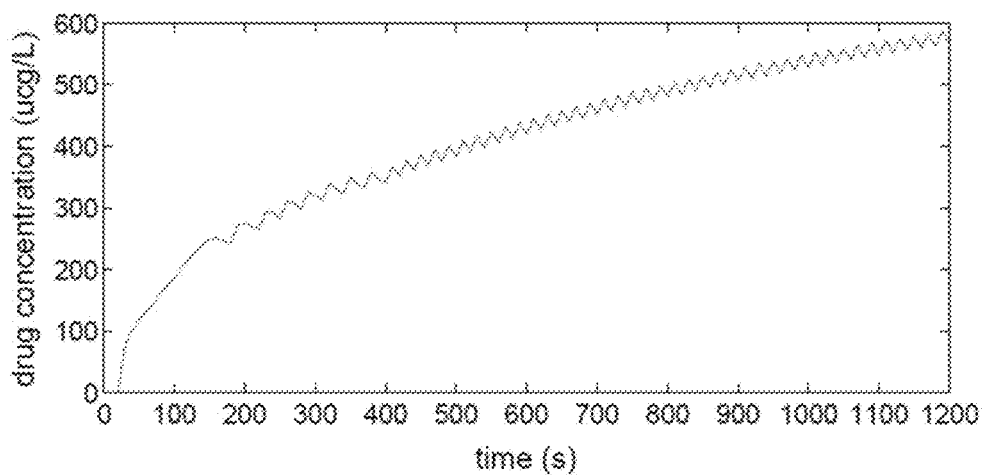
FIG. 3B is a graph of drug concentration in human blood over time as controlled by a finite domain time diffusion (FDTD) spatiotemporal model-based control algorithm implemented by the system of FIG. 1.

FIG. 3A shows an example of drug concentration in a patient's blood when the infusion pump is regulated using a pharmacokinetic model. FIG. 3B shows an example of drug concentration in a patient's blood when the infusion pump is regulated using a more complex Finite Domain Time Diffusion (FDTD) spatiotemporal modeling technique. The pharmacokinetic model is computationally less complex, but can result in a notable overshoot and undershoot of the target drug concentration as illustrated in FIG. 3A. The FTDT-based model is shown to have more accuracy and more control over drug concentrations. However, the FTDT-based model is computationally more complex and may require a longer computation time. Therefore, the system may not meet the high throughput requirements and may not be able to provide feedback to support the real time operational requirements.

Critical medical applications such as the infusion-pump-based blood-glucose control system described above must execute the prediction within a very small time window on the order of 10 seconds or less. Often the applications require estimation of the human physiology for as long as an hour in the future as feedback. However, existing computer systems force medical professionals to compromise. By selecting the less complex modeling algorithm, the drug/glucose concentration can significantly overshoot or undershoot a target concentration (as shown in FIG. 3A). However, the more complex modeling algorithm may not be able to complete execution in time to provide the required feedback—resulting in delayed actuator adjustments (as shown in FIG. 3B).

The high-throughput requirements of model-predictive control algorithms can be achieved using many-core processing platforms that can monitor several patients at the same time. The systems and methods described below meet the FLOP requirements of the application for an individual patient and also for a number of patients support simultaneously by exploiting parallelism of application at a thread level, data level, and spatial and temporal locality as well as matching the selected modeling technique to an appropriate architecture level parallelism.

Figure 4A:
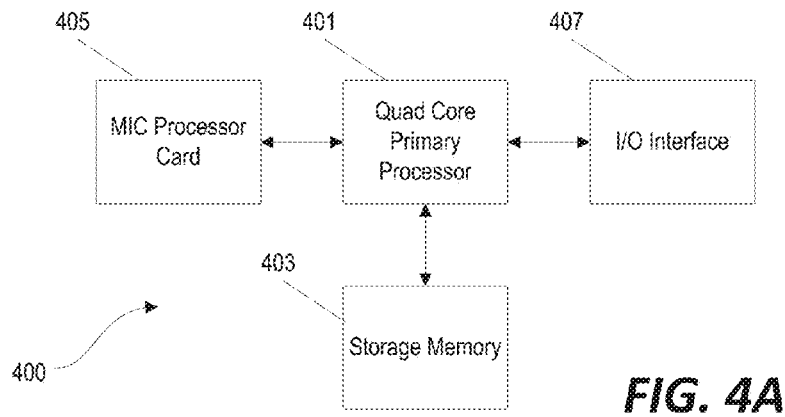
FIG. 4A is a block diagram of a heterogeneous multicore parallel processing system of the system of FIG. 1.

FIG. 4A illustrates a heterogeneous multicore parallel processing system 400 that is designed to provide predictive model-based control simultaneously for multiple patients by mapping predictive operations to an appropriate processing platform based on the modeling technique to be used and current system load. The system 400 includes a quad-core primary processor 401 with an advanced instruction set and highly sophisticated pipelining techniques. As such, the primary processor 401 is best suited for primarily serialized computer operations. The system also includes a many-core processing system 405 that is better suited for parallelized data operations. As described in further detail below, the parallelized processing system 405 may include, for example, a "Many Integrated Core" System ("MICS") or a graphics processing unit (GPU). The system 400 also includes a storage memory 403 that stores various data including, for example, instructions that are executed by the processors, input data from patient systems (see, e.g., FIG. 1), and data that results from the modeling operations. The system communicates with external monitoring systems and local communication controllers through an I/O interface 407.

Figure 4B:
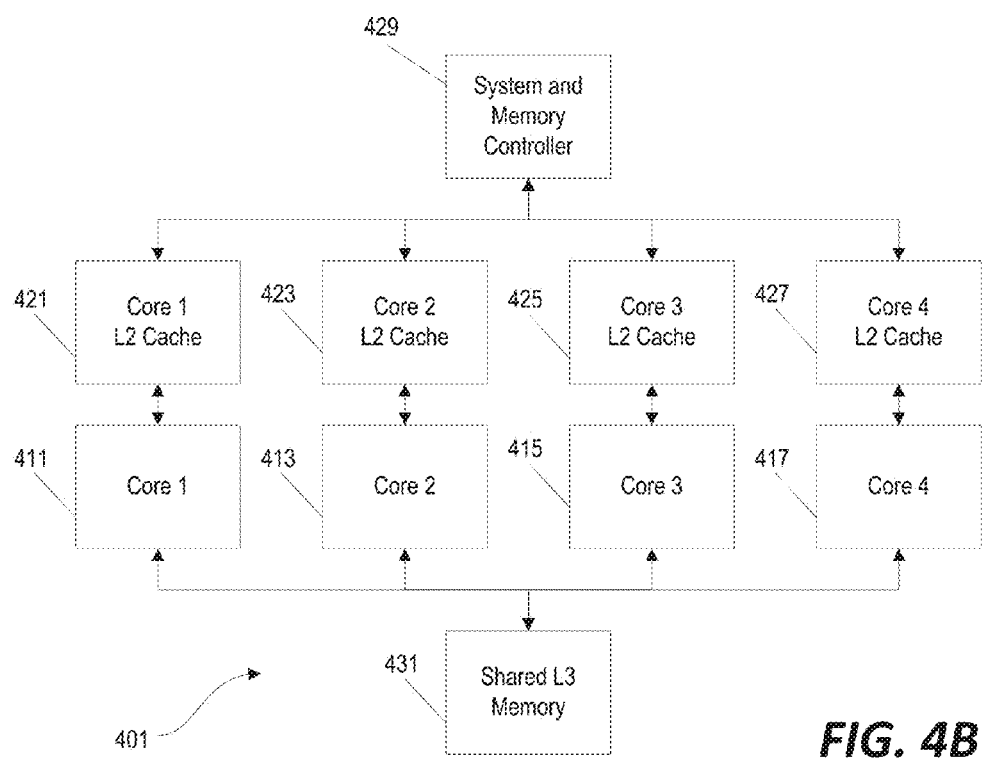
FIG. 4B is a block diagram of a quad-core, primarily serialized processing component of the heterogeneous multicore parallel processing system of FIG. 4A.

FIG. 4B illustrates one example of the primarily serialized processor 401 in further detail. The processor system 401 includes four cores 411, 413, 415, 417 each with an associated L2 cache 421, 423, 425, 427. A system and memory controller 429 controls the routing of data operations to each processing core 411, 413, 415, 417 and also regulates memory accesses. The processor system 401 also includes a shared L3 memory 431 that can be accessed by each of the four processing cores 411, 413, 415, 417.

In some constructions, the processor system 401 includes an Intel Ivybridge i7 quad-core processor with hyper-threading running at a nominal frequency of 3.5 GHz with DDR2—2400, 32 GB/4. It has 32 KB data cache and 32 KB instruction cache for L1 and 256 KB×8 way cache for L2. It has 8 MB L3 cache and DDR3, 2400 MHz Ram of 16 GB 4×4. The i7 demonstrates very fast performance for memory accesses through different levels of caches. Each quad core CPU can process 8 threads at a time. Therefore, a total of 16 threads can be run simultaneously.

Figure 4C:
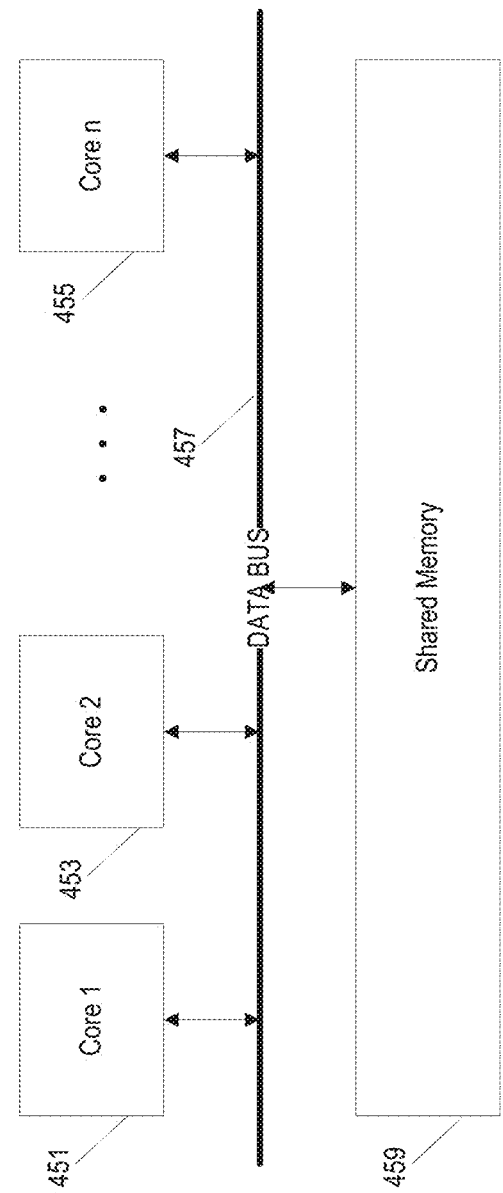
FIG. 4C is a first example of a multicore, primarily parallelized processing component of the heterogeneous multicore parallel processing system of FIG. 4A.

FIG. 4C shows a simplified version of the many core, parallelized processing platform 405. The processing system 405 includes a number of processing cores 451, 453, 455 coupled to a data bus 457 and a shared memory 459. In most processing system, a data processing bottleneck is caused by frequent memory access operations. By utilizing a relatively large shared cache memory 459, the large number of processing cores are able to quickly access the data and make changes in parallel without requiring separate memory accesses. As described in further detail below, this architecture is optimized for use with a grid-based spatiotemporal predictive modeling algorithm.

Figure 4D:
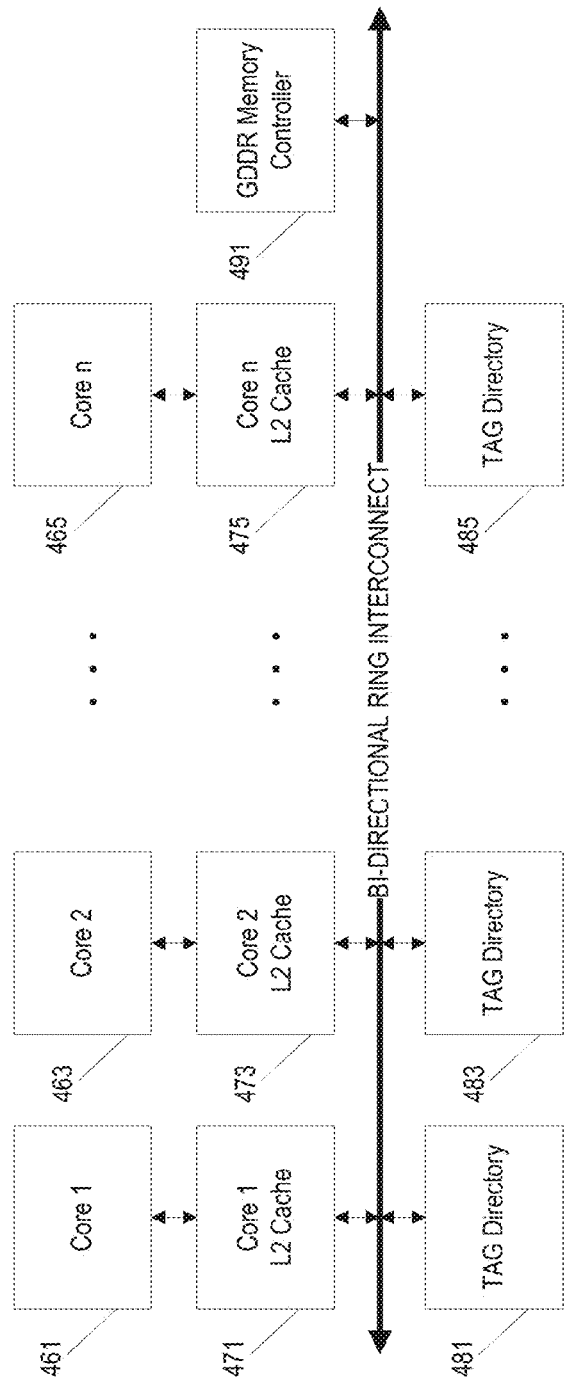
FIG. 4D is an alternative example of a multicore, primarily parallelized processing component of the heterogeneous multicore parallel processing system of FIG. 4A.

In the specific example described herein, the processing system 405 is implemented as an Intel MIC Phi controller card as illustrated in FIG. 4D. This system 405 includes 57 cores 461, 463, 465 each associated with an L2 cache 471, 473, 475. Each L2 cache has an associated tag directory 481, 483, 485 and interleaved memory controllers 491 are connected to a bidirectional ring interconnect for providing fast data from cache. Each core has a complex pipeline architecture that supports four threads. A vector processing unit (VPU) also supports Fused Multiply-Add (FMA) instructions and, therefore, can execute 32 SP or 16 DP floating point operations per cycle. The system 400 of FIG. 4A is implemented as a server with a MIC card mounted in its PCIE slot and the Intel core i7 as the host.

Although not illustrated, a graphics processing unit is another example of a many-core processing platform that could be utilized to perform highly-parallelized, basic operations. However, GPU cores are often not capable of floating-point operations and have a relatively simplistic instruction set. Therefore, a platform with many, more advanced processing cores—such as the Intel MICS—may be required for the complex mathematical modeling described in the examples herein.

This heterogeneous, multicore processing system is capable of executing multiple different predictive modeling operations for one or more patients at a time. Predictive modeling operations are routed to either the primarily serialized processing platform 401 or the primarily parallelized processing platform 405 based on factors such as the modeling technique to be utilized and the current system load. In this way, parallelism can be exploited to provide optimal system performance. Although the terms "primarily serialized" and "primarily parallelized" are used to refer to processing platform 401 and processing platform 405, respectively, it is noted that both platforms are capable of both serialized execution and parallelized execution. The terms "primarily serialized" and "primarily parallelized" are used, therefore, to distinguish between their relative performance capabilities (i.e., the Intel i7 is capable of more quickly processing highly serialized operations than the Intel MICS and the Intel MICS is capable of more quickly processing highly parallelized operations than the Intel i7).

Although the processing system 400 is capable of implementing multiple different predictive modeling operations, the examples discussed herein focus primarily on a pharmacokinetic model and a spatiotemporal model. The pharmacokinetic model represents parts of the body and shows the diffusion process to estimate the drug to be infused into the body. The transient model used here estimates the peripherally administered drug concentration at the cardiac output after a certain time by taking into account different factors such as drug entering different parts of heart and lung tissue, transport delay, recirculated blood, clearance, etc. It involves simultaneously solving the following inter-dependent time delayed differential equations, $$\dot{x}_p = A_p x_p + B_p(\dot{Q} C_s x_s(t - T_r) + u(t - T_i)), \quad (1)$$

$$\dot{x}_s = A_s x_s + B_s(\dot{Q} C_p x_p(t - T_p)), \quad (2)$$

where $x_p$ and $x_s$ represent plasma drug concentration in different parts of the body, Q is the absorption rate, $T_i$, $T_p$, $T_r$ are the drug transport delays, u(t) is infused drug level, and $A_p$, $B_p$, $A_s$, $B_s$, $C_p$, $C_s$, are constants.

The most repeated part of the pharmacokinetic algorithm involves predicting the drug concentration at the sampled point by simulation of the above infusion process with a very fine time granularity (e.g., 1 ms). Therefore, the above equations are solved simultaneously in order to obtain an accurate value of prediction. The pharmacokinetic model given by equations (1) and (2) involves solving these two equations in every time step. Each of these equations requires a series of complex mathematical operation is such as eigen value of matrix A, modal matrix and series matrix multiplications in every time step. The maximum size of matrices is 4×4 and the output of each operation is input to the next operation. Therefore, the algorithm by its nature is highly sequential. Maximally 16 threads can be processed in parallel and, hence, CPU resources required can be less.

As the size of matrices involved is relatively small, the memory requirement is low because of different temporary variables involved in the computation. The variables that are used in one stage of the processing are deleted after providing the required data to the next stage.

The data requirement of this computation does not require much communication between iterations. At the end of every stage of computation, a single floating value or small array is passed on as input to the next stage. Most of the time is consumed in waiting for input from the previous stage because of sequence of computations one after another.

FIG. 5 illustrates the method of executing the pharmacokinetic model. First, the Eigen values are calculated of 4×4 matrix A (step 501). Then a model matrix M of A is obtained (step 503) and a Jordanian J of M is determined (step 505). The exponent of J is computed (step 507) and a series of 9 matrix multiplication are performed to solve for output y(t) (step 509).

The pharmacokinetic model involves complex mathematical computations where the output of one stage is the input to the next. The iterative part of the algorithm involves computation of eigen values (step 501), building a modal matrix M (step 503), and obtaining a Jordanian on a matrix (step 505). In these complex operations, the matrices involved are of the size 4×4 and, therefore, at most 16 points are computed in parallel. Multiple threads are used to computer these 16 points simultaneously. The next operation cannot start until it receives the output value from the previous operation. Optimized libraries to perform these complex math operations such as Intel Math Kernel Library (MKL) or MAGMA library can be used.

Since there is a maximal limit of 16 threads for parallelization, on the whole, the operation is primarily serialized as opposed to parallelized. However, parallelism can be obtained by processing multiple patients simultaneously. Therefore, as discussed in further detail below, the pharmacokinetic model is naturally better suited for execution on a primarily serialized processing platform. However, optimized performance can be achieved on a primarily parallelized platform in circumstances where many patients are monitored by the same system 400.

The second modeling technique—the spatiotemporal-based FDTD algorithm—estimates and controls the drug diffused into the human tissue in the time and the space domain. This control mechanism has three modes: (a) basal, where infusion rate is $I_0$, (b) braking, where infusion rate is a fraction f of $I_0$, and (c) correction bolus, where infusion rate is incremented by $I_b$. Diffusion dynamics of the drug is spatio-temporal in nature and can be modeled using the multi-dimensional PDE equation:

$$\frac{\partial d}{\partial t} = \nabla (D \nabla d) + \Gamma (d_B(t) - d) - \lambda d, \quad (3)$$

Where d(x,t) is the tissue drug concentration at time t and distance x from the infusion site, D is the diffusion coefficient of the blood, $\Gamma$ is the blood-to-tissue drug transfer coefficient, $d_B(t)$ is the prescribed infusion rate at time t, and $\lambda$ is the drug decay coefficient. A control algorithm implementing equation (3) samples drug concentration in the blood and adjusts the infusion pump drug levels so as to achieve the desired physiological effects while avoiding hazards such as hyperglycemia.

The control algorithm, therefore, requires solving the differential equation periodically within the time interval between two control inputs. The Finite Difference Time Domain (FDTD) method is used to solve the differential equations. A double derivative in this method $$\frac{\delta^2 V}{\delta x^2}$$

can be discretized using the finite different time domain method and represented as:

$$V^{m+1}(i,j) = K \times [V^m(i+1,j) + V^m(i,j+1) + V^m(i-1,j) + V^m(i,j-1)], \quad (4)$$

Where the time is discretized into slots indexed by m, the x and y space dimensions are discretized with slots indexed by i and j, respectively, and K is a constant. The entire solution involves computation of each grid point based on the linear combination of neighboring points. For each 5 cm×5 cm area on the body with a grid size of 1 mm requires a computation of 68 FLOPs per grid point. To solve the equation using this method for 1 hour ahead in the future requires 1 TeraFLOPs.

The spatiotemporal model mechanism is a highly computational algorithm and it involves simulation of all grid points in order to estimate the drug level in the tissue for every second into the future. As discussed above in reference to equation (4), every grid point involves a window-type operation of the grid values of previous iterations. Using the neighboring grid points, new values of the grid are computed. As every grid value involves 68 FLOPs computations, the number of computations increases with the grid size.

If the entire grid is available in cache, the computations can take advantage of the parallelized processing techniques. If the grid data is divided and cached for computation, it will need to be combined together after the computation, processed with a few serial operations, and then sent back for the grid computation. Depending on the location of cached data, data from all the grid points is compiled in order to do serial processing before it is again divided into chunks and sent for processing in parallel. This may incur much data transfer overhead in each iteration.

In the spatiotemporal model, the most repeated part is the computation of grid point values using neighboring gird points from the previous iteration. FIG. 6 shows the flow of computations involved. The grid size is defined (step 601) and three versions of the N×N giver matrix are created and maintained (step 603). Each point in the grid is computed/updated using equation (4) (step 605) and then grid matrices are updated (step 607). For a grid size G×G, all points are computed in parallel using the previous grid data.

A fully parallelized form of this model involves computing the entire grid using G×G threads. However, the nature of the algorithm is such that it includes a few serial processes at the end of each iteration. As a result, new updated grid values have to be used for computation in the next iteration. Vector processing is used to enhance the performance of the sequential accesses in the grid block or the data chunks.

Some processing platforms may impose a high overhead of data transfer in order to concentrate the grid data, perform serial processes, and then disperse the data for parallel processing. Computation on GPU is overlapped on the communication to save time. However, the data transfer overhead for GPU platforms is much higher. In contrast, the entire grid data fits into the memory for the MIC and i7 platforms and, therefore, memory access overhead is greatly reduced.

As discussed above, certain predictive modeling techniques—such as the pharmacokinetic model—are highly serial in nature and do not provide for optimized parallel processing. However, due to the complex mathematical operations involved, execution times would benefit significantly from the advanced instruction set and processing capabilities of the quad-core processor. Conversely, the relatively large grid/matrix computations involved in the spatiotemporal model lend themselves well to the parallel processing capabilities of a more parallelized processing platform such as the MIC.

As such, the primary processor 401 of FIG. 4A—as the host processor—determines the type of modeling to be performed and routes the operation to the appropriate processing platform. As illustrated in FIG. 7, when a new modeling operation is initiated (step 701), the system determines whether the modeling technique used is primarily parallel (step 703). If so, the modeling operation is executed by the MIC processor (step 705). If the modeling technique to be used is primarily serialized, then the modeling operation is executed by the quad-core processor (step 707).

Figures 8, 11:
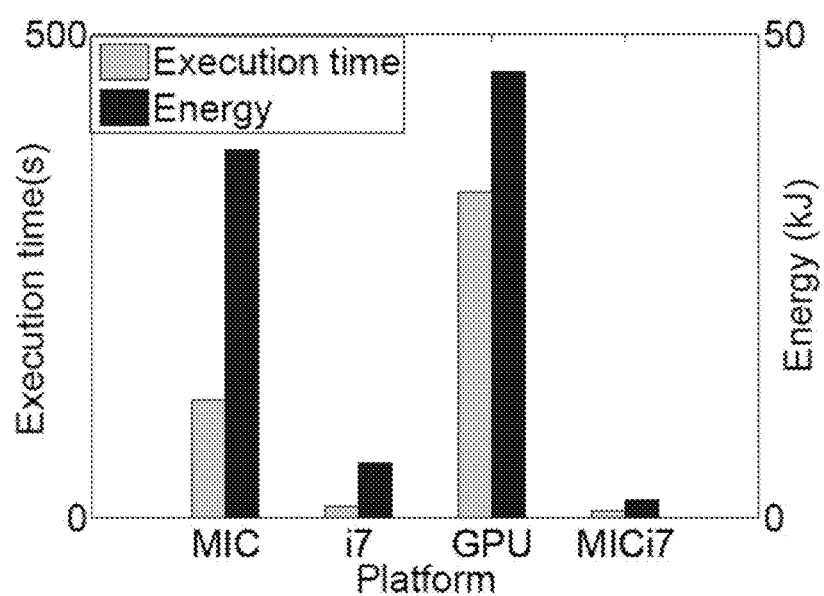
FIG. 8 is a table of measured execution times for the predictive algorithm of FIG. 5 executed by various processing platforms for various numbers of patients.
FIG. 11 is a graph of energy and performance metrics for various processing platforms each monitoring multiple patients and executing a combination of the predictive algorithm of FIG. 5 and the predictive algorithm of FIG. 6.

Routing the modeling operation to a processing architecture that better matches its computational characteristics results in significant performance benefits. The highly serialize implementation of the pharmacokinetic model results in poor performance on multicore platforms as illustrated in FIG. 8. The table of FIG. 8 shows the execution times for half hour simulations of pharmacokinetic model data for different numbers of patients on the i7 platform, the MIC platform, and the GPU platform. As shown, the performance of the pharmacokinetic model on the i7 platform is far superior to the GPU and MIC for relatively low numbers of patients. The reason for such a superior performance is the fast cores in the i7 and supporting pipeline vector processing compared to relatively slow individual cores of the GPU and MIC platforms. In spite of the high computational capabilities of the GPU and the MIC, the other computer resources cannot be utilized because of the highly sequential operations involving 4×4 matrices that can only utilized 16 threads at a time.

In contrast, the tables of FIGS. 9 and 10 show the performance of the spatiotemporal model in terms of execution time in different sizes of tissue (i.e., a grid size of 2 mm) a half hour after it is infused for multiple patients on each example platform. As discussed above, the spatiotemporal model involves parallel computation followed by serial processing. The data grid is divided into chunks and sent for parallel processing, gathered for serial processing, and the cycle continues for every iteration. Since there can be a large data transfer overhead for gathering the data to the host side, specifically for platforms such as the GPU, FIG. 9 illustrates the execution time involving (1) computation and data transfer and (2) involving only computation.

The table of FIG. 9 and the table of FIG. 10 show the performance of the control algorithm for two grid data sizes, 64×64 and 256×256, respectively. As illustrated, computation on the MIC platform is completed relatively fast as the data need not be sent to the host device in every iteration. Platforms like the MIC with large cache access and a high number of computation devices (i.e., cores) are architecturally suited for applications that involve both serial and parallel computations. In contrast, the data transfer overhead of the GPU platform is much higher as indicated by comparing the "computation only" execution time to the "computation and communication" execution time in FIGS. 9 and 10. As shown in the last two columns of each table, the execution time is more than doubled for the GPU platform. Execution times for the i7 platform are reasonable for a smaller number of patients. However, as the number of patients increases, the computational time increases rapidly.

The energy and the performance results for the Pharmacokinetic model for different phases of the code is shown in the table of FIG. 12. The energy consumption is excluding the idle power of the machine. The serial nature of the code makes use of the powerful cores in i7 incurring much less time in the data communication and also faster computations. The FLOPs per Joules for the i7 platform also indicates that the i7 will be more useful for such applications involving complex math computation but lesser degree of parallelism. The spatiotemporal code seems to utilize the computation capability of the multi core platforms. Considering the table of FIG. 13, if 64 patients are being monitored simultaneously, almost 45 TFlops need to be computed before the infusion time. The subsequent columns show the energy consumption and the performance of application on different platforms. As seen in the table of FIG. 13, the MIC platform gives better performance for our application considering the FLOPs/Joule are much higher whereas GPU and i7 are comparable considering the computation of serial parts in the code involves large communication overhead.

The tables of FIGS. 8, 9, 10, 12, and 13 provide execution data for performing only a single type of modeling on a single processing platform. These results seem to indicate that the pharmacokinetic model will run more efficiently and faster on the i7 platform while the spatiotemporal application preforms exceedingly well on the MIC platform. However, in a real hospital scenario, different patients will be monitored with different modeling techniques based on the criticality and need of the patient.

For example, as discussed above, the pharmacokinetic modeling technique is less computationally intensive, but can result in overshooting and undershooting a target drug concentration level. Therefore, the pharmacokinetic modeling technique may be sufficient for patients that are not exhibiting any signs of criticality. However, critical patients that are particularly susceptible to the adverse effects of overshooting or undershooting a target drug concentration are preferably monitored using the more computationally intensive spatiotemporal model.

In some systems, the medical professional will select which modeling technique is to be used for a specific patient. However, in other constructions, the system may be configured to automatically determine whether to use the pharmacokinetic model (i.e., a "slow response" model) or the spatiotemporal model (i.e., a "fast response" model) based on monitored physiological patient data. For example, a patient whose monitored vital signs indicate distress would be shifted to the spatiotemporal model and, when the vital signs stabilize, would be shifted back to the pharmacokinetic model.

FIG. 11 illustrates the relative execution time and energy consumption of the MIC platform, the i7 platform, and the GPU platform while monitoring three patients under the pharmacokinetic model and 16 patients using the spatiotemporal model. These results initially seem to indicate that the parallel processing capability of the MIC and GPU platforms cannot compensate for speed of the i7 quad-core platform as both the execution time and the energy requirements of the MIC and GPU platforms far exceed the i7. However, FIG. 11 also shows that the heterogeneous system of FIG. 4A—including both the MIC processing platform (i.e., the primarily parallelized platform) and the i7 processing platform (i.e., the primarily serialized platform)—results in both reduced execution time and energy savings.

Therefore, in some constructions, as discussed above, the system is configured to route primarily parallelized modeling operations to the primarily parallelized platform (i.e., spatiotemporal modeling to the MIC platform) while primarily serialized modeling operations are routed to the primarily serialized platform (i.e., pharmacokinetic modeling to the i7 platform). However, as illustrated in FIGS. 8-10, execution times will increase as the number of patients monitored by the system increases. Therefore, returning to FIG. 7, in some constructions, even the primarily serialized modeling operations may be routing to the primarily parallelized processor when multiple patients are being monitored by the same system (step 709).

When a certain number of patients being monitored by the system is exceeded, the processing speed benefits of the i7 processing platform are outweighed by the parallelized processing capabilities of the MIC platform. Therefore, when performance benefits of the i7 platform begin to decrease due to the volume of patient being monitored according to the pharmacokinetic model, the system will shift the modeling operations to the MIC platform to exploit the parallelism benefits due to monitoring multiple patients in parallel.

In some constructions, this operation routing is achieved by defining a threshold number of patients that can be monitored using the primarily serialized technique before shifting the operations to the parallelized processing platform. However, in other constructions, a dynamic look-up table is maintained that defines the effect on execution time of adding a new modeling operation to either the primarily serialized processing platform or the primarily parallelized platform also accounting for the type of modeling technique to be utilized for the new modeling operation. The system will then route the new operation to the processing platform that will result in the lowest increase in average execution time.

Figure 14:
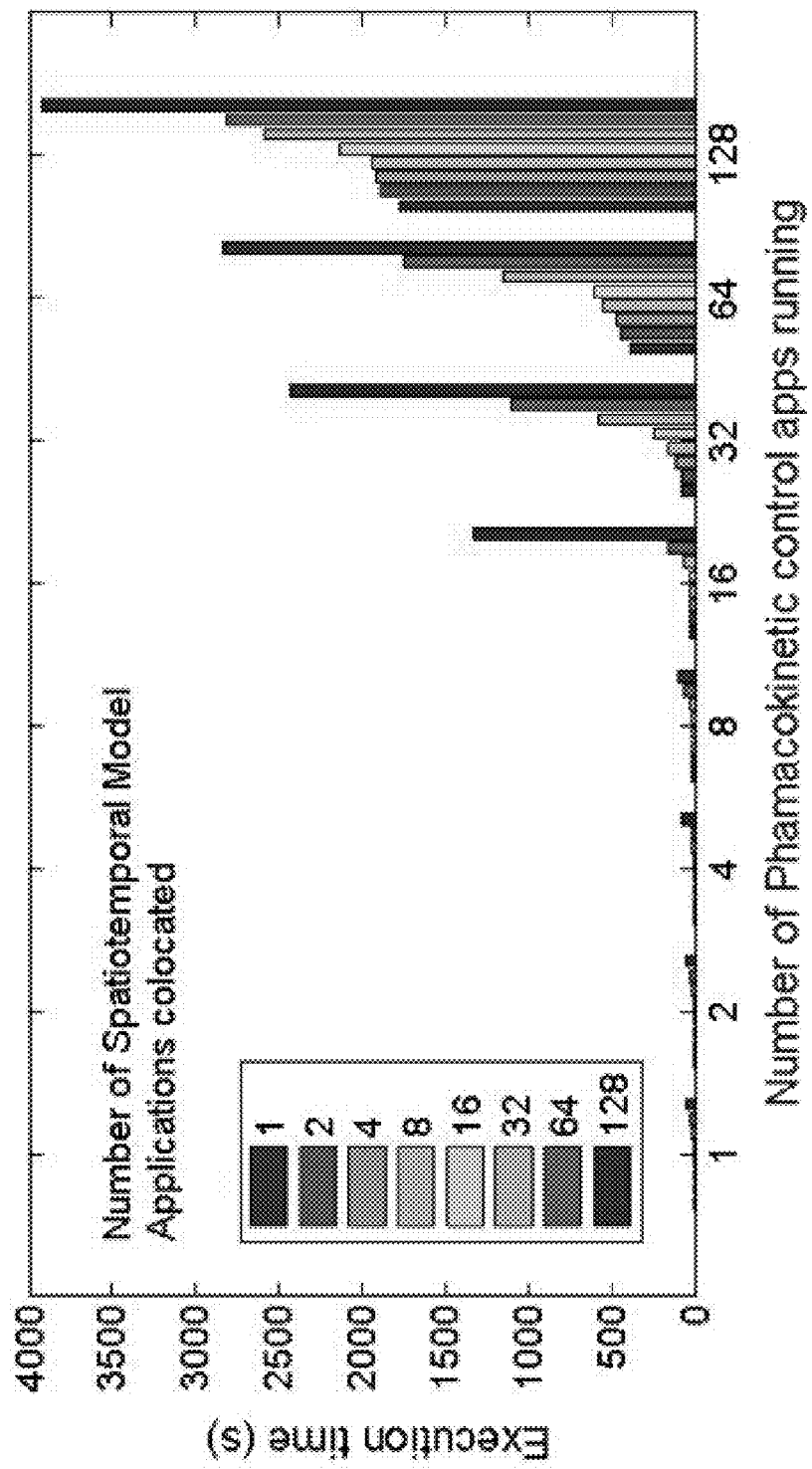
FIG. 14 is a graph of model iteration execution times on a first processor platform for various combinations and numbers of concurrent modeling applications.
Figure 15:
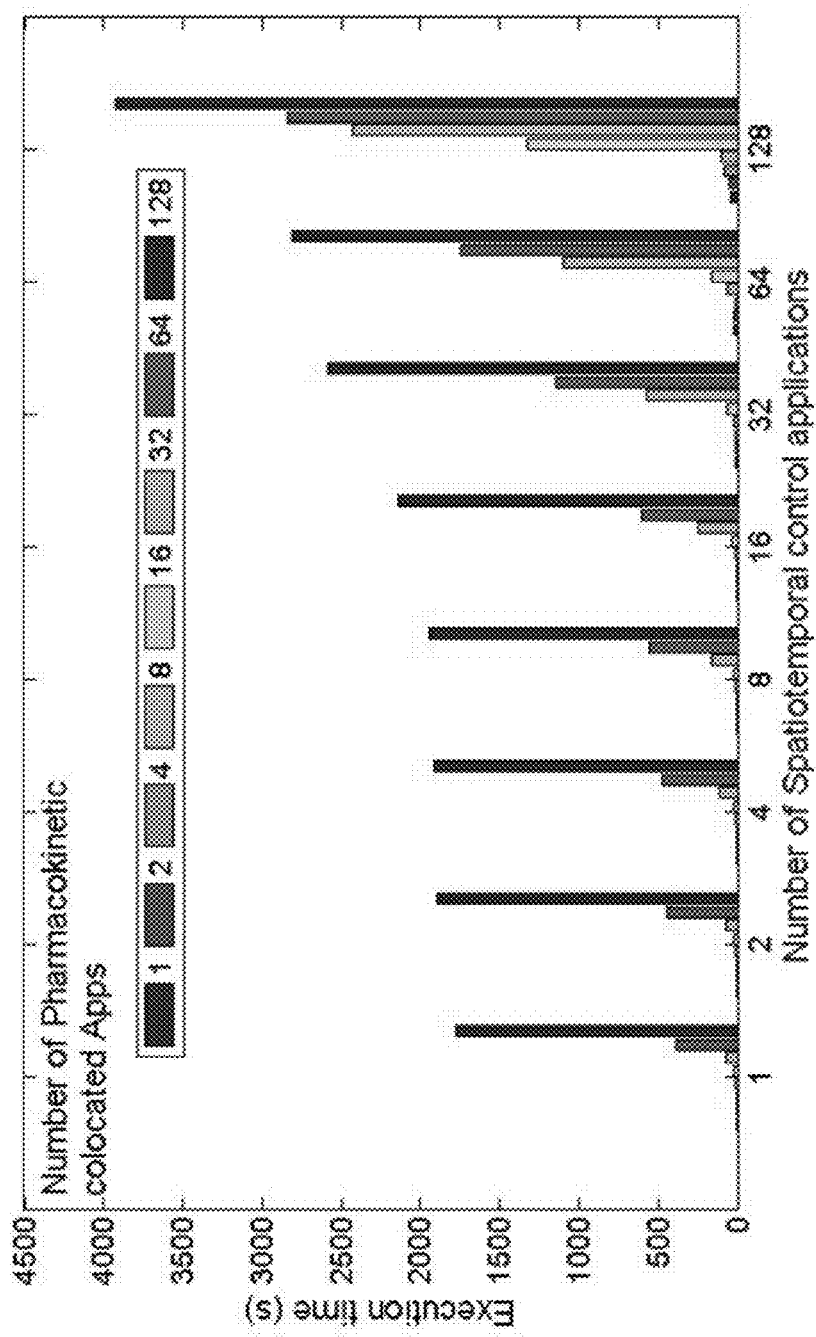
FIG. 15 is a graph of model iteration execution times on the first processor platform for various combinations and numbers of concurrent modeling applications.
Figure 16:
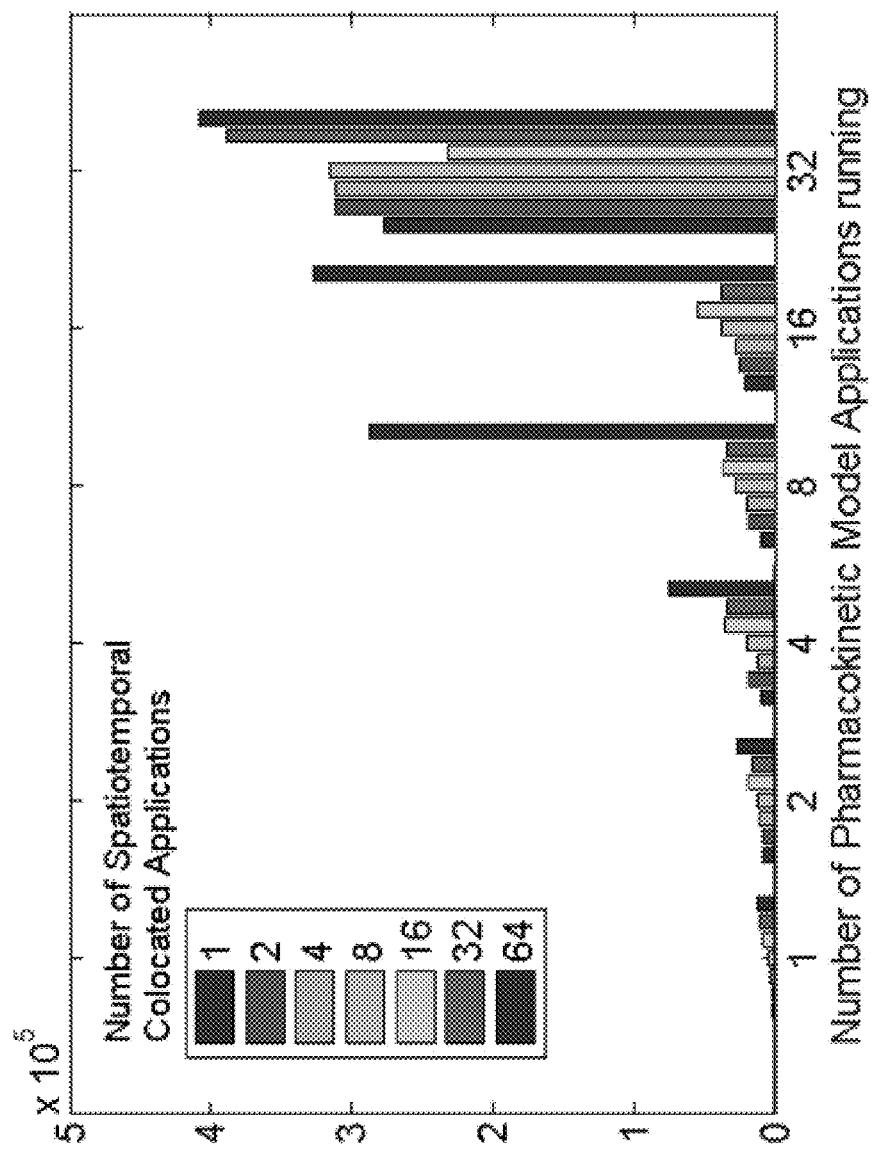
FIG. 16 is a graph of model iteration execution times on a second processor platform for various combinations and numbers of concurrent modeling applications.
Figure 17:
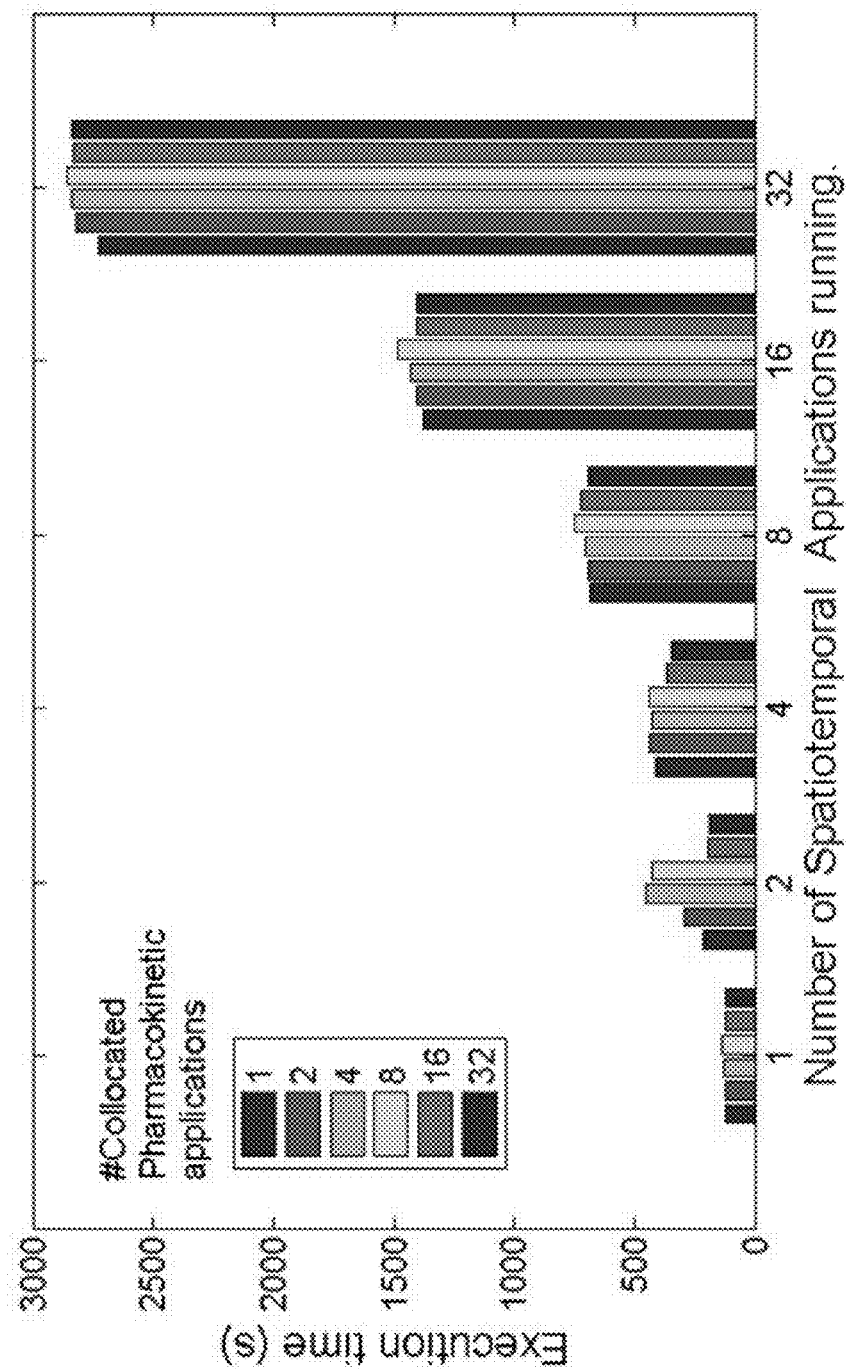
FIG. 17 is a graph of model iteration execution times on the second processor platform for various combinations and numbers of concurrent modeling applications.
Figure 18:
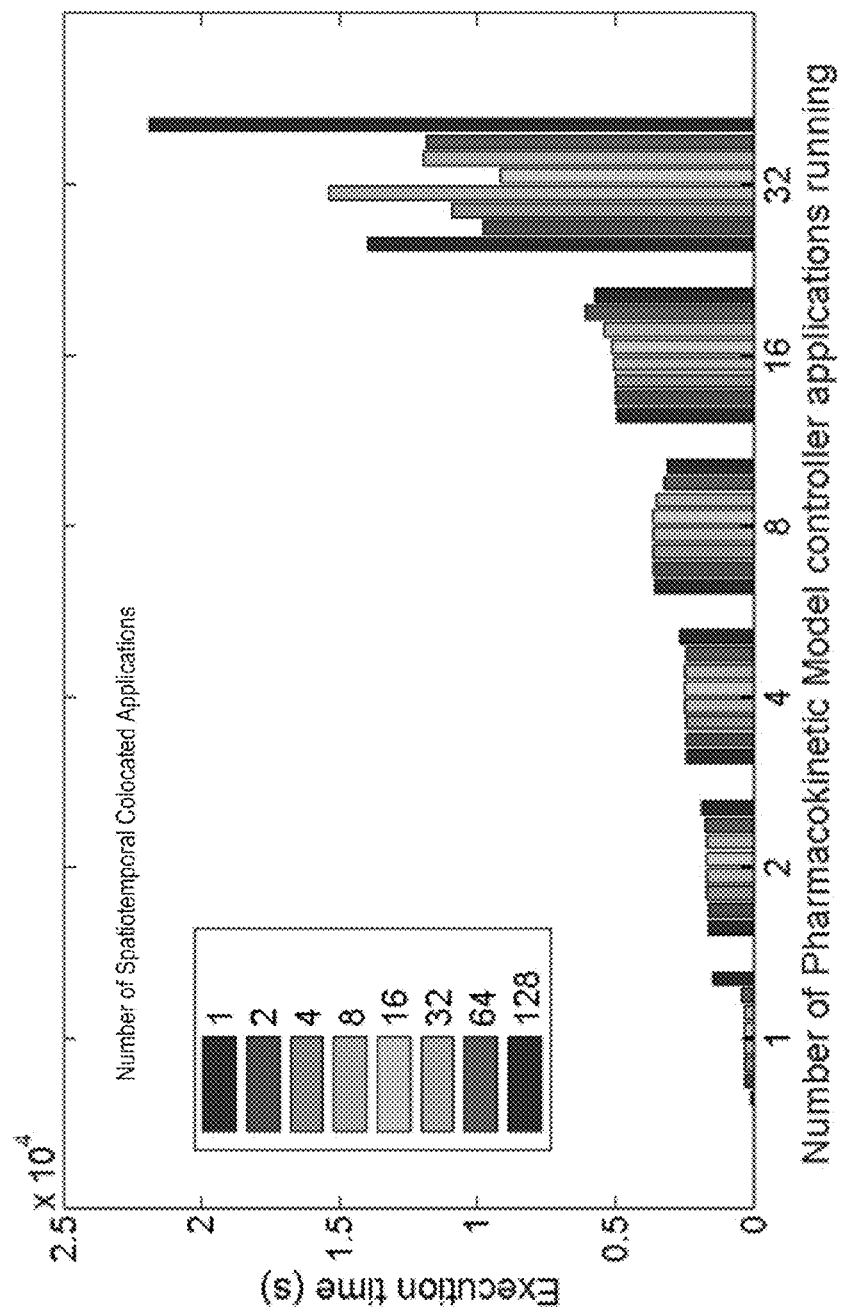
FIG. 18 is a graph of model iteration execution times on a third processor platform for various combinations and numbers of concurrent modeling applications.
Figure 19:
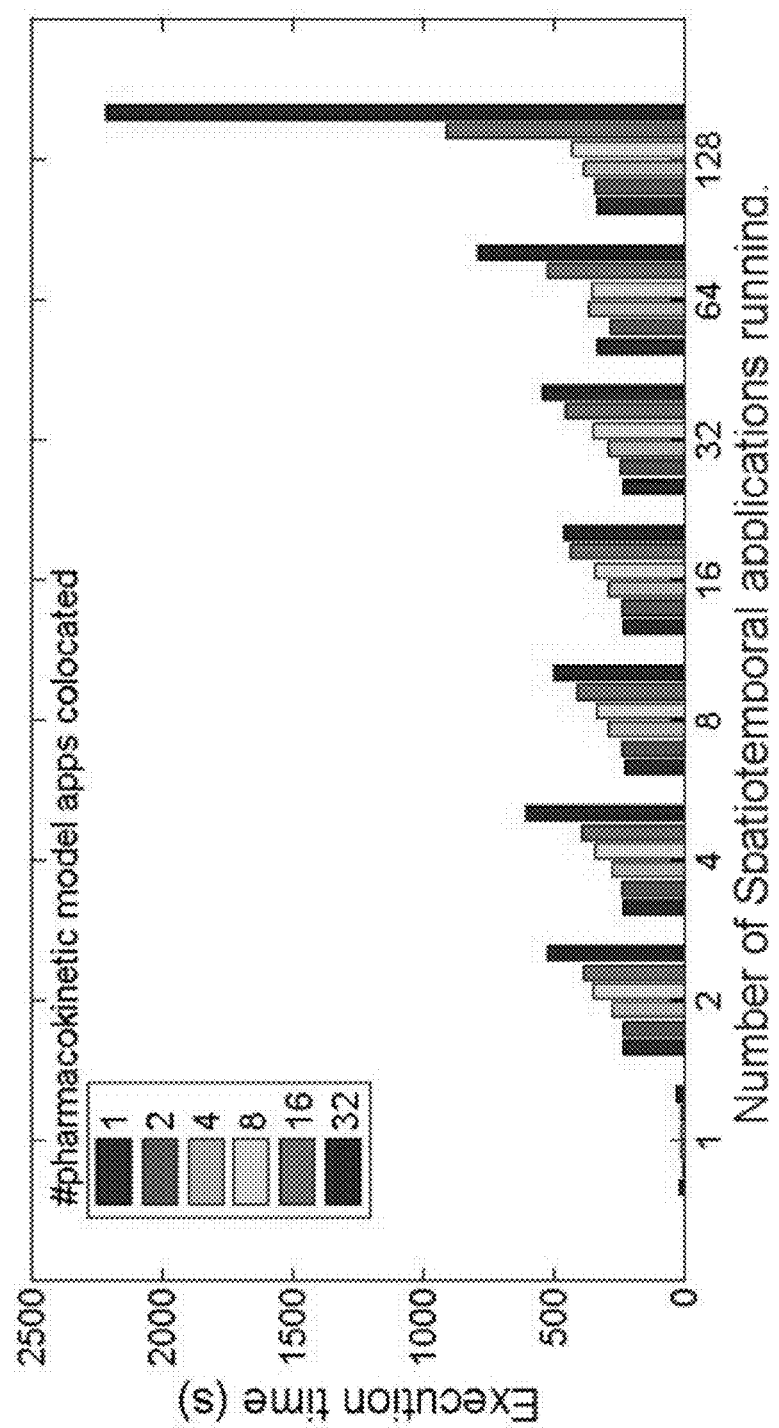
FIG. 19 is a graph of model iteration execution times on the third processor platform for various combinations and numbers of concurrent modeling applications.

FIGS. 14-19 illustrate examples of such look-up tables in bar graph form. FIG. 14 illustrates the execution time for a number of concurrently executed pharmacokinetic model applications running on an i7 processing platform. Each bar indicates a number of spatiotemporal model applications that are also concurrently executed on the same i7 processing platform. FIG. 15 also illustrates execution times on the i7 platform; however, the number of concurrent spatiotemporal modeling applications are shown on the x-axis and the number of pharmacokinetic modelings are illustrated by the corresponding bars. FIGS. 16 and 17 illustrate the execution times on a MIC processing platform for various combinations of spatiotemporal and pharmacokinetic modelings while FIGS. 18 and 19 illustrate the execution times on a GPU processing platform.

When a new modeling application is initiated on the system, the system consults the look-up tables and, based on the current workload executed on the various processing platforms, the system determines which processing platform can execute the new modeling application with the smallest increase in average execution time. For example, if the system includes an i7 processing platform and a MIC processing platform (as discussed in the examples above) and the system is currently running (a) 128 spatiotemporal modelings and 4 pharmacokinetic modelings on the MIC platform and (b) 64 pharmacokinetic modelings on the i7 platform, then the system will conclude—based on the look-up tables illustrated in FIG. 14 and FIG. 19—that the average execution time for adding a new pharmacokinetic modeling application to the MIC processor will be less (just under 500 s) than adding the new pharmacokinetic modeling application to the i7 processor (just over 500 s). Therefore, even though the pharmacokinetic modeling application is generally a primarily serial process, the new pharmacokinetic modeling application would be routed to the MIC processing platform for execution.

Thus, the invention provides, among other things, a heterogeneous multicore processing platform that executes predictive modeling algorithms according to a primarily parallelized algorithm or a primarily serialized algorithm and routes new modeling operations to either a primarily parallelized processing platform or a primarily serialized platform based on the type of modeling technique to be utilized and current system load. Various features and advantages of the invention are set forth in the following claims.

What is claimed is:

1. A heterogeneous multiple core control system for predictive medical monitoring comprising:
   a first processor platform optimized for serialized computation;
   a second processor platform optimized for parallelized computation; and
   a memory storing instructions that, when executed by the first processor platform and the second processor platform, cause the system to
      determine whether a condition of a first patient is to be monitored using a primarily parallelized model or a primarily serialized model,
      calculate a predicted condition of the first patient using the primarily parallelized model by executing the primarily parallelized model on the second processor platform, and
      calculate the predicted condition of the first patient using the primarily serialized model by executing the primarily serialized model on the first processor platform; and
   wherein the instructions, when executed by the first processor platform and the second processor platform, further cause the system to monitor a first change in average execution time resulting from adding a new patient monitored using the primarily serialized model on the first processor platform, and monitor a second change in average execution time resulting from adding a new patient monitored using the primarily serialized model on the second processor platform, and wherein the instructions, when executed by the first processor platform and the second processor platform, cause the system to calculate the predicted condition of the first patient using the primarily serialized model by executing the primarily serialized model on the first processor platform when the first change in average execution time is less than the second change in average execution time, and executing the primarily serialized model on the second processor platform when the second change in average execution time is less than the first change in average execution time.

2. The heterogeneous multiple core control system of claim 1, wherein the instructions, when executed by the first processor platform and the second processor platform, further cause the system to monitor a plurality of patients, wherein a first number of patients are monitored using the primarily parallelized model and a second number of patients are monitored using the primarily serialized model.

3. The heterogeneous multiple core control system of claim 2, wherein the instructions, when executed by the first processor platform and the second processor platform, cause the system to calculate the predicted condition of the first patient using the primarily serialized model by executing the primarily serialized model on the first processor platform when the second number of patients monitored using the primarily serialized model is less than a threshold, and executing the primarily serialized model on the second processor platform when the second number of patients monitored using the primarily serialized model is greater than the threshold.

4. The heterogeneous multiple core control system of claim 1, wherein the primarily serialized model is computationally less intensive than the primarily parallelized model and requires more iterations than the primarily parallelized model to reflect changes in the monitored condition.

5. The heterogeneous multiple core control system of claim 1, further comprising sensors to monitor the concentration of an infused drug in the patient's body.

6. The heterogeneous multiple core control system of claim 1, wherein the predicted condition is a future concentration of the infused drug in the patient's body.

7. The heterogeneous multiple core control system of claim 6, wherein the instructions, when executed by the first processor platform and the second processor platform, further cause the system to determine an adjusted infusion amount based on the predicted future concentration, and provide a control instruction to an infusion pump causing the infusion pump to operate based on the adjusted infusion amount.

8. The heterogeneous multiple core control system of claim 1, wherein the first processor platform includes a lower number of processing cores than the second processor platform and operates at a higher execution speed than the second processor platform.

9. The heterogeneous multiple core control system of claim 1, further comprising a controller board, wherein the controller board includes the second processor platform.

10. The heterogeneous multiple core control system of claim 1, wherein the primarily serialized model includes a pharmacokinetic drug diffusion model.

11. The heterogeneous multiple core control system of claim 1, wherein the primarily parallelized model includes a Finite Domain Time Diffusion model.

12. The heterogeneous multiple core control system of claim 1, wherein the primarily parallelized model includes a grid identifying drug concentrations at different anatomical locations of the first patient, wherein the grid is stored in a cache memory accessible by each processing core of the second processor platform, and wherein each iteration of the primarily parallelized model of the plurality of parallel processing cores accesses a plurality of predicted values from the grid and calculates a new value for a specific anatomical location.

13. A heterogeneous multiple core control system for predictive medical monitoring comprising:
a first processor platform optimized for serialized computation;
a second processor platform optimized for parallelized computation; and
a memory storing instructions that, when executed by the first processor platform and the second processor platform, cause the system to
determine whether a condition of a first patient is to be monitored using a primarily parallelized model or a primarily serialized model,
calculate a predicted condition of the first patient using the primarily parallelized model by executing the primarily parallelized model on the second processor platform, and
calculate the predicted condition of the first patient using the primarily serialized model by executing the primarily serialized model on the first processor platform
wherein the instructions, when executed by the first processor platform and the second processor platform, further cause the system to monitor a plurality of patients, wherein a first number of patients are monitored using the primarily parallelized model and a second number of patients are monitored using the primarily serialized model, and wherein the instructions, when executed by the first processor platform and the second processor platform, further cause the system to balance a number of patient monitored by executing a model on the first processing platform and a number of patients monitored by executing a model on the second processing platform to reduce an average execution time.

14. The heterogeneous multiple core control system of claim 13, wherein the primarily serialized model is computationally less intensive than the primarily parallelized model and requires more iterations than the primarily parallelized model to reflect changes in the monitored condition.

15. The heterogeneous multiple core control system of claim 13, further comprising sensors to monitor the concentration of an infused drug in the patient's body.

16. The heterogeneous multiple core control system of claim 13, wherein the predicted condition is a future concentration of the infused drug in the patient's body.

17. The heterogeneous multiple core control system of claim 16, wherein the instructions, when executed by the first processor platform and the second processor platform, further cause the system to determine an adjusted infusion amount based on the predicted future concentration, and provide a control instruction to an infusion pump causing the infusion pump to operate based on the adjusted infusion amount.

18. The heterogeneous multiple core control system of claim 13, wherein the first processor platform includes a lower number of processing cores than the second processor platform and operates at a higher execution speed than the second processor platform.

19. The heterogeneous multiple core control system of claim 13, further comprising a controller board, wherein the controller board includes the second processor platform.

20. The heterogeneous multiple core control system of claim 13, wherein the primarily serialized model includes a pharmacokinetic drug diffusion model.

* * * * *